United States Patent [19]
Oberhoffner et al.

[11] Patent Number: 6,031,069
[45] Date of Patent: Feb. 29, 2000

[54] TRIBLOCK TERPOLYMER, ITS USE IN MEDICAL PRODUCTS AND PROCESS FOR ITS PRODUCTION

[75] Inventors: Sven Oberhoffner, Weinstadt-Benzach; Heinrich Planck, Nuertingen, both of Germany

[73] Assignee: Duetsche Institute fuer Textil- und Faserforschung Stuttgart Stiftung des oeffentlichem Rechts, Germany

[21] Appl. No.: 08/967,386

[22] Filed: Oct. 8, 1997

[30] Foreign Application Priority Data

Oct. 8, 1996 [DE] Germany ............................ 196 41 334

[51] Int. Cl.⁷ ............................................ C08G 63/08
[52] U.S. Cl. ..................... 528/354; 528/357; 528/361; 606/230; 521/189
[58] Field of Search ...................... 528/354, 357, 528/361, 480, 481; 606/230; 521/189

[56] References Cited

U.S. PATENT DOCUMENTS

| | | | |
|---|---|---|---|
| 3,839,524 | 10/1974 | Adams et al. | 264/131 |
| 4,933,430 | 6/1990 | Kessler et al. | 528/323 |
| 5,047,048 | 9/1991 | Bezwada et al. | 606/231 |
| 5,120,802 | 6/1992 | Mares et al. | 525/415 |
| 5,133,739 | 7/1992 | Bezwada et al. | 606/230 |
| 5,321,113 | 6/1994 | Cooper et al. | 528/176 |
| 5,411,554 | 5/1995 | Scopelianos et al. | 623/8 |
| 5,431,679 | 6/1995 | Bennett et al. | 606/230 |
| 5,550,172 | 8/1996 | Regula et al. | 523/118 |
| 5,713,920 | 2/1998 | Bezwada et al. | 606/230 |
| 5,854,383 | 12/1998 | Erneta et al. | 528/354 |

FOREIGN PATENT DOCUMENTS

| | | |
|---|---|---|
| 0 098 394 A1 | 1/1984 | European Pat. Off. . |
| 0 441 322 A1 | 8/1991 | European Pat. Off. . |
| 0 626 404 A2 | 11/1994 | European Pat. Off. . |
| 0 711 548 | 5/1996 | European Pat. Off. . |
| 0 711 794 | 5/1996 | European Pat. Off. . |
| 0 719 811 | 7/1996 | European Pat. Off. . |
| 0 747 072 | 12/1996 | European Pat. Off. . |
| 43 00 420 | 7/1994 | Germany . |
| 1 571 108 | 9/1980 | United Kingdom . |
| 1 588 031 | 4/1981 | United Kingdom . |
| 2 122 228 | 11/1984 | United Kingdom . |
| 2 159 846 | 12/1985 | United Kingdom . |
| WO 94/11441 | 5/1994 | WIPO . |

*Primary Examiner*—Mark L. Warzel
*Attorney, Agent, or Firm*—Pennie & Edmonds LLP

[57] ABSTRACT

A resorbable polymer suitable for producing a medical product, comprising a triblock terpolymer with a structure ABA formed from a biodegradable hard segment A and a biodegradable soft segment B, has as the soft segment a statistical terpolymer with a completely amorphous structure. A process for its production comprises chemically reacting the hard segment monomer with hydroxy terminal groups of the soft segment B. The resorbable medical product produced from the triblock terpolymer can be a textile fabric, produced from multifilaments, a film, membrane or an injection molding.

15 Claims, No Drawings

TRIBLOCK TERPOLYMER, ITS USE IN MEDICAL PRODUCTS AND PROCESS FOR ITS PRODUCTION

TECHNICAL FIELD

The present invention relates to a triblock terpolymer of absorbable synthetic polymer, its use in surgical suture material and processes for the production thereof.

BACKGROUND OF THE INVENTION

Absorbable synthetic polymers usable for medical products such as e.g. surgical suture material or implants, include conventional homopolymers of polyglycolic acid or polylactic acid, as well as their copolymers. Particularly in the case of suture materials monofilament products have the advantage compared with braided multifilament structures, that they have a smooth, homogeneous surface. This facilitates the course of the thread ard reduces the occurrence of capillarities. Thus, no coatings need be applied in order to improve the compactness of the thread.

A disadvantage of the known polymers for suture material is their high flexural strength, partly linked with an inadequate transverse tensile strength, which leads to a poor knotting behaviour and limits the use for surgical sutures.

Therefore developments have led to the use of block copolymers, e.g. the structure AB, ABA or ABAB, in which at least one block constitutes a so-called soft segment. It is known to produce soft segments by homopolymerization or copolymerization of monomers, such as e.g. trimethylene carbonate (1,3-dioxan-2-one) TMC, ε-caprolactone or p-dioxanone (1,4-dioxan-2-one). The soft segments are reacted with hard segments, whose monomers are typically chosen from glycolide and/or lactide, to the corresponding block copolymers.

Among the commercially marketed long term-absorbable suture materials reference is made to the block copolymer of glycolide and trimethylene carbonate disclosed in European patent 98394 A1 of the American Cyanamid Company.

A crystalline copolymer of glycolide and ε-caprolactone described in

European patent EP 441322 A1 of ETHICON Inc. constitutes a short term-absorbable polymer material.

European patent EP 626404 A2 of United States Surgical Corporation (USSC) claims absorbable block copolymers of glycolide, p-dioxanone and trimethylene carbonate, in which the soft segment is formed solely from p-dioxanone and TMC.

U.S. Pat. No. 5,431,679 of United States Surgical Corporation describes a block copolymer, which comprises a block of glycolide ester units and a block of statistical copolymers of 1,3-dioxan-2-one and caprolactone.

The problem of the present invention is to provide an absorbable synthetic polymer in the form of a triblock terpolymer, which has a good degradation and absorption behaviour in vivo combined with good mechanical characteristics, which is easy and inexpensive to manufacture and which can be easily and reliably used for medical products.

SUMMARY OF THE INVENTION

This problem is solved by a triblock terpolymer with a structure ABA of a biodegradable hard segment A and a biodegradable soft segment B, in which the soft segment B is dihydroxy-terminated and to it is chemically bound both hard segments and which is characterized in that the soft segment is a statistical terpolymer with a completely amorphous structure.

The completely amorphous structure of the soft segment can advantageously influence the in vivo degradability. The degradation behaviour of the soft segment approaches that of the hard segment. With regards to the structural features there is also an increased compatibility of soft segment and hard segment. This leads to a balanced absorption behaviour in vivo of the hard and soft segments in the triblock terpolymer.

The structure of the triblock terpolymers according to the invention has an advantageous effect on the characteristics of products produced there from. Examples are favourable mechanical characteristics such as good flexibility, e.g. low flexural strength, good modulus behaviour and good knotting characteristics, such as are in particular desired in applications in the medical sector.

DETAILED DESCRIPTION OF THE INVENTION

In the triblock terpolymer according to the invention the hard segment A can in particular be a homopolymer. In the case of the triblock terpolymer the terpolymer in the soft segment B can contain a monomer, which is contained in the hard segment A. Advantageously, in the block terpolymer, the percentage of hard segment blocks A is 20 to 95 wt. %, particularly 20 to 80%, preferably 40 to 60 wt. % of the triblock terpolymer and the residue is soft segment B.

The triblock terpolymer in the soft segment B can be characterized in that it is formed from trimethylene carbonate, ε-caprolactone and glycolide. In particular, trimethylene carbonate can be contained in a percentage of 5 to 70 wt. %, ε-caprolactone in a percentage of 5 to 70 wt. % and glycolide in a percentage of 10 to 70 wt. % in the terpolymer according to the invention. The percentages by weight of the components trimethylene carbonate, ε-caprolactone and glycolide are chosen in such a way that together they represent 100 wt. % of the terpolymer in the soft segment B. According to the invention, the triblock polymer in the terpolymer preferably contains 10 to 40 wt. % trimethylene carbonate, 10 to 40 wt. % ε-caprolactone and 30 to 60 wt. % glycolide.

In the terpolymer of the soft segment B according to the invention can be present trimethylene carbonate and ε-caprolactone in a weight ratio between 80:20 and 20:80, particularly 70:30 and 30:70. The soft segment terpolymer preferably contains trimethylene carbonate and ε-caprolactone in a weight ratio of 50:50. In another embodiment the soft segment terpolymer can contain ε-caprolactone in a higher proportion than trimethylene carbonate.

The triblock terpolymer according to the invention is in particular characterized in that the monomer present both in the hard segment A and the soft segment B is glycolide. Preferably the terpolymer of the soft segment B is produced by statistical copolymerization of trimethylene carbonate, ε-caprolactone and glycolide.

In the trilock terpolymer acconge invention advantageously the soft segment B, as the middle block, is surrounded on either side by hard segment blocks A. The hard segment is attached to both ends of the soft segment by polymerization reaction at the OH-groups. The formation of the hard segment can advantageously take place by reacting the OH-terminated soft segment terpolymer with glycolide monomers. A triblock terpolymer strand according to the invention preferably comprises only one soft segment in the polymer strand.

Tests of the physical and physiological characteristics of the triblock terpolymer according to the invention were performed, such as e.g. the microstructure, glass transition range, melting behaviour, inherent viscosity, biodegradability and resorption behaviour. Unless stated other wise viscosity measurements take place in hexafluoroisopropanol (HFIP) at 30° C. and a concentration of c=0.8 g/dl. Measurements of the glass transition temperatures (Tg), melting points (Tm) and melting enthalpies (Hm) are performed by differential scanning calorimetry (DSC).

The triblock terpolymer according to the present invention differs from the conventional block polymers hitherto used e.g. for the production of surgical suture material as a result of the modified sequence of the monomer Lnits in the macromolecular chain. This also influences the interactiors between the individual chain molecules in a filament or moulding formed. As is well known to experts in the fibre technology field, the physical and mechanical characteristics of a fibre are dependent on the orientation and structure of the chain molecules, particularly the formation of amorphous and crystalline ranges.

Preferably, the triblock terpolymer has an inherent viscosity of 0.5 to 1.5 dl/g, particularly 0.7 to 1.2 dl/g. The triblock terpolymer according to the invention can also have a glass transition temperature or point between −10° C. and +25° C. Preferably, the soft segment B in the triblock terpolymer according to the invention has a glass transition point between −30° C. and +10° C. In particular, the triblock terpolymer is characterized in that its structure is partly crystalline, the crystallinity being limited to the hard is segment. The melting enthalpy, a measure for the crystallinity of a polymer in the case of the triblock terpolymer according to the invention is between 15 and 50 J/g.

The absorbable triblock terpolymer according to the invention is advantageously characterized by an accelerated absorbability in living tissue. Its in vitro degradation time can be 5 to 30 days (Sorensen buffer, 37° C.).

It is to be assumed that the incorporation of a third monomer in random distribution in the soft segment reduces the crystallization tendency of the soft segment. In fact, tests by differential scanning calorimetry (DSC), reveals that the soft segment B is completely amorphous in the structure. A suppression of the crystallization in the soft segment leads to a desired improvement to the flexibility of products produced from the triblock terpolymer according to the invention.

The degradation of the polymer according to the invention takes place in the body of an animal or human by metabolic processes. Body and tissue fluids participate in the reaction. As a result of hydrolysis the polymer chain is split up into smaller and more readily soluble fragments. The fragments are then further degraded, optionally accompanied by the participation of enzymatic processes. The degradation products are transported away by the metabolic system and, in the same way as other metabolic waste products, are eliminated from the organism. It is important for a good compatibility of the absorbable suture material with respect to the patient, that during the degradation process no harmful metabolites are formed or concentrated. Polyglycolic acid is in particular characterized that during its decomposition in vivo no toxic decomposition products are formed. The trimethylene carbonate and caprolactone used as comonomers according to the invention are also characterized by a good compatibility and the avoidance of toxic reactions.

Compared with glycoide, trimethylene carbonate and caprolactone have much longer degradation times. This can lead to a widely differing absorption behaviour of hard segment (e.g. glycolide) and soft segment (e.g. TMC/ caprolactone copolymer according to the prior art). Incompatible polymers or polymer segments have a phase separation tendency, which generally leads to a deterioration of the mechanical strength.

By polymerizing glycolide into the soft segment it is possible to increase the compatibility between the hard segment and the soft segment. This has an advantageous effect on the mechanical characteristics of the polymer important in practice. This can also lead to a more uniform degradation and absorption of the soft and hard segments of the block copolymers in the living organism.

The degradation behaviour of the triblock terpolymer according to the invention can be modified by varying the overall glycolide percentage in the polymer. The degradation behaviour of the triblock terpolymer according to the invention can also be modified by varying the percentage of soft segment B in the triblock terpolymer. Another influencing factor, through whose variation it is possible to modify the degradation behaviour in the inventive polymer, is the intensity and duration of any γ radiation. Treatment with γ rays can be linked with a partial molecular weight deterioration, which leads to shortened degradation times. It is possible in this way to adapt the characteristics of the triblock terpolymer according to the invention to the advantageous requirements in the individual case. In a possible embodiment of the invention, a sterilization performed with the aid of γ rays can be simultaneously used for controlling the degradation behaviour of the medical products produced from the polymer according to the invention.

It has been found that the triblock terpolymer with a structure ABA formed from a hard segment A of biodegradable monomer and a soft segment B of biodegradable monomer, in which the soft segment is a statistical dihydroxytermirated terpolymer with an amorphous structure, is suitable as an absorbable polymer for producing a medical product. The product provided for medical use is then advantageously wholly or partly formed from the polymer.

It has surprisingly been found that medical products can be produced from the bLock polymer according to the invention, particularly monofilaments for suture material, which have the very good characteristics necessary for surgical material, particularly with respect to the physical properties and practical handling.

Examples are products for medical applications such as implants in the form of textile fabrics, film or sheet material, membranes or mouldings.

In preferred embodiments the triblock terpolymer according to the invention can be used as an implant in the form of an injection moulded product. In a particularly preferred use, the polymer can be used as an anastomosis ring produced by injection moulding. Other preferred uses are e.g. products in the form of clips, clamps, suture rings or dowels.

The triblock terpolymer according to the invention can also be used as an implanti in the form of a textile fabric. This can be in the form of a woven, knitted or braided fabric, a nonwoven or an interlaid scrim and can e.g. serve as a patch for tissue regeneration. Another preferred use of the triblock terpolymer is a medical product in the form of a microporous membrane. Another preferred use of the triblock terpolymer is a medical product in the form of a film.

As is apparent from the above description of the characteristics of the polymer according to the invention, it is in particular characterized by its biodegradability and favourable degradation behaviour, together with its good mechanical characteristics, especially its flexibility, for applications in the medical sector.

The present invention also provides a process for the production of a triblock terpolymer with a structure ABA formed from a hard segment A of biodegradable monomer and a soft segment B of biodegradable monomer, which is characterized in that the triblock terpolymer is formed by chemically reacting the hard segment monomer with hydroxy terminal groups of the soft segmeit B, which is a statistical, dihydroxy-terminated terpolymer with an amorphous structure.

More particularly, in the case of the production process according to the invention, the soft segment can be produced by statistical copolymerization of trimethylene carbonate, ϵ-caprolactone and glycolide, with 5 to 70, preferably 10 to 40 wt. % trimethylene carbonate, 5 to 70, preferably 10 to 40 wt. % ϵ-caprolactone and 10 to 70, preferably 30 to 50 wt. % glycolide. The percentages by weight of the components trimethylene carbonate, ϵ-caprolactone and glycolide are chosen in such a way that, together, they represent 100 wt. % of the terpolymer in the soft segment B.

The monomer mixture for producing the soft segment according to the invention can have added to it in the conventional necessary quantity, a suitable catalyst, such as e.g. tin octoate, as well as a bifunctional initiator, e.g. diethylene glycol. The reaction is performed as a melt polymerizatior. at temperatures above 150° C. in a suitable heatable reactor equipped with a stirrer. In particular, this polymerization reactor must be designed in such a way that the resulting highly viscous melts are homogenized, the requisite temperature ranges can be respected and the raw polymer can be substantially completely discharged from the reactor.

The terpolymerization reaction can be performed according to standard procedures, known to the expert, for the production of statistical copolymers. Preferably, the reaction mixture is heated, accompanied by constant thorough mixing, particularly to a temperature of 190 to 210° C., preferably 205° C. For the duration of the reaction, an overpressure of 1 to 2 aid preferably 1.5 bar argon is applied. For a reaction duration of 2 to 6 hours, preferably 5 hours, the preintroduced monomers can react to a statistical terpolymer. Advantageously, the process is characterized in that the reaction rate during soft segment polymerization is above 95%.

In an embodiment of the process according to the invention, the soft segment can be isolated after polymerization and reacted to the triblock terpolymer following repeated melting on with glycolide. For this purpose, at the end of the reaction, the raw terpolymer of the soft segment B is discharged as melt and comminuted after cooling.

The reaction of the soft segment terpolymer with glycolide monomer to the triblcck terpolymer takes place in known manner as a melt polymerization in a suitable polymerization reactor, as described hereinbefore for the production of the soft segment. Once again it is possible to add in the standard, necessary quantity a suitable catalyst, e.g. tin octoate, as well as a bifunctional initiator, e.g. diethylene glycol. Preferably, the reaction mixture is heated for a period of 0.5 to 1 hour to a temperature of 200 to 250° C., preferably 220 to 240° C. The switching in of a stirrer preferably takes place after reaching a temperature of approximately 130° C. For the duration of the reaction an overpressure of 1 to 2 and preferably 1.5 bar argon is applied. During the reaction period of 1 to 3 hours, the triblock terpolymer with hard and soft segments of structure ABA is formed. Subsequently the polymer is discharged from the reactor and, after cooling, is comminuted and dried in the usual way.

In another embodiment of the process according to the invention, after polymerization the soft segment can be directly reacted in situ with glycolide the triblock terpolymer. The in situ polymerization of the tri-block terpolymer according to the invention takes place as melt polymerization in a polymerization reactor, as described hereinbefore for the aforementioned polymerization reactions. Firstly the monomers glycolide, 1,3-dioxan-2-one and caprolactone are added to the reactor in the quantities necessary for soft segment formation, together with the necessary catalyst and initiator. Accompanied by stirring, the mixture is heated at an argon overpressure of 1 to 2 bar for approximately 30 min to a temperature of 200 to 210° C. and is reacted under these conditions for 4 to 6 hours. For forming the triblock terpolymer, a requisite quantity of the hard Eegment monomer glycolide is added as melt. Reaction for hard segment formation takes place under an argon counterflow and accompanied by vigorous stirring. The temperature is increased in less than 15 min to approximately 230° C., is then reduced to approximately 220° C. and these conditions are maintained until the reaction is completed for approximately 1 to 2 hours, The finished triblock terpolymer is discharged and, after cooling, comminuted and dried in the conventional manner.

Using conventional melt spinning or injection moulding processes, resorbable medical products can be produced from the triblock terpolymers according to the invention. In an embodiment of the process the triblock terpolymer can be formed by injection moulding to a moulded part.

Preferably the triblock terpolymer according to the invention can be injection moulded to an anastomosis ring.

Resorbable multifilaments can be produced by conventional melt spinning processes from the triblock terpolymers according to the invention. In a preferred embodiment the triblock terpolymer can be extruded in a melt spinnirg process, e.g. a single-screw extruder or twin-screw extruder, througt suitable spinning nozzles to multifilaments. During melt spinning the nozzle temperature is in particular up to 30° C. above the melting point of the polymer to be processed.

Advantageously, the filament formed is extruded in an air-supplied cooling section or in a cooling bath, which contains water or a conventional, organic liquid, such as e.g. glycerin. The cooling temperature can be in the raige 2 to 50° C. Preference is given to extrusion at ambient temperature. The distance between the spinning nozzle and the cooling section is between 0.5 and 30 cm, preferably between 1 and 10 cm.

In order to obtain the necessary mechanical characteristics, the extruded filament can be stretched or drawn for orienting the molecular chains. The strengthened spinning thread can either be drawn directly or, following winding up or spooling, in a separate step using standard methods. It is possible to carry out drawing either in heated, liquid media such as e.g. water or glycerin baths, or using drawing ovens and rails. Advantageously it car be drawn with a draw ratio of 1:4 to 1:10.

In order to ensure a permanent maintenance of the orientation, the mechanical characteristics and the dimensional stability, the stretched or drawn polymer material can be set or fixed by annealing. Setting takes place at temperatures in the range 50 to 150° C., preferably 70 to 130° C. The heat setting process duration is between 1 and 20 hours.

Annealing can take place with or without shrinkage of the filament. It is particularly preferable for drawing and heat setting to take place immediately following extrusion, particularly using a combined process. Advantageously, for this purpose, use is made of a corresponding equipment constituted by combined, suitable devices. In a preferred embodiment of the invention the products produced from the triblock terpolymer can be exposed for 1 to 20 hours, with or without shrinkage, to a temperature of 50 to 150° C. in order to obtain dimensional stability.

The diameter of the single filaments produced in this way can be in the range 0.001 to 0.05 mm. There can be between 3 and 1000 filaments.

It is possible to produce from the triblock terpolymers according to the invention films by extrusion with slot dies, the extrudate being strengthened by means of a cooling bath (water or organic liquids such as e.g. glycerin in the aforementioned temperature range), followed by calendering. The thickness of the films is between 0.015 and 1.5 mm.

Membranes of the triblock terpolymers according to the invention can be produced in the following ways:

a) Production of pores in the aforementioned films by energy supply using laser or ultrasonics.

b) By phase inversion technology, for which purpose the triblock terpolymer is dissolved in a suitable solvent (e.g. hexafluoroisopropanol, trifluoroacetic acid or with a lower overall glycolide proportion, e.g. in chloroform) and is then coagulated in a precipitant on suitable devices. The precipitant must be completely mixable with the solvent.

c) By freeze drying technology, in which the viscous polymer solution is coated e.g. by means of a doctor blade onto a carrier and immediately frozer. By drawing off the solvent in vacuum, the desired pores are formed.

Injection mouldings such as anastomosis rings or dowels from the triblock terpolymer according to the invention are obtained under similar extrusion conditions to those for multifilament production. As a function of the mould geometry higher pressures of up to several hundred bars are needed. Preferably working takes place with an after-pressure to avoid shrinkage. Through clearly defined mould temperatures and cooling rates, e.g. 1 to 5° C./min, it is possible to control the crystallinity of the products and minimize stresses in the component. The moulding can be tempered or conditioned in order to obtain a permanent dimensional stability.

The polymers and medical products produced therefrom according to the present invention can be dyed or undyed. For dyeing purposes, it is possible to use the dyes authorized for absorbable, medical devices by the US FDA (Food and Drug Administration), such as e.g. D+C green No. 6, D+C violet No. 2, etc.

Medical products produced from triblock terpolymer according to the invention can be sterilized in an appropriate manner using conventional methods. An appropriate sterilization process can be chosen from conventional physical or chemical methods for deactivating microorganisms, or a combination of such methods. A possible sterilization process comprises the treatment with radiation. Preferably the sterilization of the polymer material according to the invention for medical products takes place using ethylene oxide.

Due to the hydrolytic decomposability of the polymer material according to the intention medical products, during the storage thereof, must be protected against moisture and elevated temperatures, so that the strength characteristics are fully maintained up to the time of use. Advantageously, medical suture threads produced according to the invention, are packed in ready-for-use state in dried form. Appropriately this can be brought about by a moisture-proof pack, particularly a pack of moisture-impermeable film material, preferably as a vacuum pack. It is also achievable by the choice of a dry, cool storage location.

The polymers according to the invention and the products produced therefrom are in particular characterized by the following physical properties. It is a semicrystalline triblock polymer, which is consequently solid at ambient temperature and which has a firm consistency. The triblock polymer has a melting point above 120° C. There is no phase separation between the hard and soft segments. This is apparent from the glass transition temperature, which for the terpolymer according to the invention is −10 to +30° C., particularly 0 to +15° C. With several phases, separate detectable glass transition points would exist.

The inherent viscosity of the triblock terpolymer according to the invention is advantageously above 0.7 dl/g in HFIP (c=0.8 g/l at 30° C.). The inherent viscosity can be up to 2.0 dl/g for polymers usable in practice.

So that in the polymer according to the invention the residual monomer content is low and simultaneously a high reaction or transformation rate is obtained, the soft segment polymerization in the melt can take place at over 10° C., preferably above 170° C., up to 235° C.

In the case where the polymer according to the invention is transformed into threads and is in particular drawn or stretched, the knot breaking strength changes during the degradation period. After 7 days it is between 30 and 80%, preferably between 50 and 70% of the original value. After 14 days the knot breaking strength is still between 5 and 50%, particularly between 20 and 40% of the original value, as is apparent from measurements in the Sorensen buffer at pH 7.4 and 37° C.

Moreover, with the drawn polymer material according to the invention, particularly drawn threads, the elongation is between 15 and 60%, preferably between 25 and 45%. The linear tensile strength is between 300 and 1000 N/mm$^2$, particularly above 400 N/mm$^2$. The knot tensile strength is between 250 ard 800 N/mm$^2$, preferably above 350 N/mm$^2$.

For the triblock polymer according to the invention the modulus of elasticity is between 500 and 3000 N/mm$^2$, preferably below 1800 N/mm$^2$. In the case of multifilament threads modulus of elasticity values can be up to 7000 N/mm$^2$, preferably less than 5000 N/mm$^2$.

EXAMPLES

Further features and details of the invention can be gathered from the following description of preferred, exemplified embodiments. The individual features can be implemented individually or in the form of subcombinations. The examples merely serve to illustrate the present invention, which is in no way restricted thereto.

Example 1

Dihydrcxy-terminated soft segment of composition G/TMC/CL=30/35/35.

In a reactor are placed 350 g of 1,3-dioxan-2-one (TMC), 350 g of caprolactone (CL) and 30 g of glycolide (G), together with 0.2 g of tin octanoate (si)lution in diethyl ether) and 1 g of diethylene glycol. The ether is then drawn off in high vacuum at 50° C. After 1 hour an overpressure of 1.5 bar argon is applied and the reactor heated to 205° C., accompanied by stirring. This temperature is maintained for 5 hours, after which the polymer is discharged and analyzed. The inherent viscosity is 0.648 dl/g, and the glass transition point −27.5° C.

Example 2

Dihydroxy-terminated soft segment of composition G/TMC/CL=40/30/30.

To a reactor are added 300 g of 1,3-dioxan-2-one, 300 g of caprolactone and 400 g of glycolide, together with 0.2 g of tin octanoate (solution in diethyl ether) and 1 g of diethylene glycol. The reaction to the polymer takes place in the same way as in example 1. The inherent viscosity is 0.937 dl/g and the glass transition temperature −19.8° C.

Example 3

Dihydroxy-terminated soft segment of composition G/TMC/CL=50/25/25.

To a reactor are added 250 g of 1,3-dioxan-2-one, 250 g of caprolactone and 500 g of glycolide, together with 0.2 g of tin octanoate (solution in diethyl ether) and 1 g of diethylene glycol. The reaction takes place as in example 1. The inherent viscosity is 0.813 dl/g and the glass transition point −9.3° C.

Example 4

Triblock terpolymer of composition G/TMC/CL=72/14/14 with 40 wt. % of soft segment from example 1.

To a reactor are added 600 g of glycolide and 400 g of the soft segment of example 1, together with 0.1 g of tin octanoate (solution in diethyl ether) The ether is drawn off in high vacuum at 50° C. After applying an overpressure of 1.5 bar argon, the reactor is heated for 40 min to 240° C. The switching in of a stirrer takes place on reaching a temperature of 130° C. The temperature of 240° C. is maintained for 70 min and the polymer is the discharged. The inherent viscosity of the ABA triblock terpolymer is 0.75 dl/g, the glass transition point is 9.5° C. and the melting point is 182.3° C.

Example 5

Triblock terpolymer of composition G/TMC/CL=73/13.5/13.5 with 45 wt. % of the soft segment of example 2.

550 g of glycolide and 450 g of the soft segment from example 2, without additional catalyst addition, are placed in the reactor and dried in high vacuum at 60° C. for 16 hours. After applying an overpressure of 1.5 bar argon, the reactor is heated to 235° C. for 35 min, the stirrer being switched in on reaching a temperature of 130° C. The temperature of 235° C. is maintained for 60 min and the polymer is then discharged.

The inherent viscosity of the ABA triblock terpolymer is 1.01 dl/g, the glass transition temperature 9.8° C. and the melting point 180.1° C.

Example 6

Triblock terpolymer of composition G/TMC/CL=73/13.5/13.5 with 54 wt. % soft 3segment of example 3.

460 g of glycolide and 540 g of the soft segment from example 3, together with 0.05 g of tin octanoate (solution in diethyl ether) are placed in the reactor and dried in high vacuum for 16 hours at 50° C. After applying an overpressure of 1.5 bar argon, the reactor is heated for 45 min to 230° C., the stirrer being switched in on reaching a temperature of 130° C. After 10 min the temperature is reduced to 220° C. and kept at this level for 100 min. The polymer is then discharged.

The inherent viscosity of the ABA triblock terpolymer is 0.813 dl/g, the glass transition temperature 9.9° C. and the melting point 164.5° C.

Example 7

In situ polymerization of a triblock terpolymer of composition G/TMC/CL=73/13.5/13.5 with 45 wt. % of a soft segment of composition G/TMC/CL=40/30/30.

In the first stage, 360 g of glycolide, 270 g of 1,3-dioxan-2-one and 270 g of capolactone, together with 0.9 g of diethylene glycol and 0.2 g of tin octanoate (solution in diethyl ether) are placed in the reactor. After drying for 16 h at 50° C. in high vacuum, an overpressure of 1.5 bar argon is applied and the reaction mixture is heated, accompanied by stirring, for 30 min to 205° C. This temperature is maintained for 5 h. In stage 2 there is an addition of 1100 g of melted glycolide for forming hard segments, under an argon counterflow and with vigorous stirring. Simultaneously the temperature is raised for 10 min to 230° C., then lowered to 220° C. and kept there for 90 min.

The polymer has an inherent viscosity of 1.02 dl/g, the glass transition point is 2.1° C. and the melting point 191.2° C. A sample of the soft segment taken prior to glycolide addition has an inherent viscosity of 1.081 dl/g and the glass transition point is −20.1° C.

Example 8

In situ polymerization of a triblock terpolymer of composition G/TMC/CL=73/13.5/13.5 with 54 wt. % of a soft segment of composition G/TMC/CL=50/25/25.

In the first stage, 540 g of glycolide, 270 g of 1,3-dioxan-2-one and 270 g of caprolactone, together with 1.08 g diethylene glycol and 0.216 g of tin octanoate (solution in diethyl ether) are placed in the reactor. After trying for 16 h at 50° C. in high vacuum, an overpressure of 1.5 bar argon is applied and the reaction mixture is heated to 205° C. for 30 min, accompanied by stirring. This temperature is maintained for 5 h. In stage 2 1100 g of melted glycolide are added for forming the hard segments, under an argon counterflow and accompanied by vigorous stirring. Simultaneously the temperature is raised for 10 min to 230° C., then lowered to 220° C. and kept there for a further 80 min.

The polymer has an inherent viscosity of 0.99 dl/g, a glass transition point of 10.4° C. and a melting point of 183.6° C.

Example 9

In situ polymerization of a triblock terpolymer of composition G/TMC/CL=44/28/28 with 80 wt. % of a soft segment of composition G/TMC/CL=30/35/35.

In the first stage, 480 g of glycolide, 560 g of 1,3-dioxan-2-one and 560 g of caprolactone, together with 1.60 g of diethylene glycol and 0.320 g of tin octanoate (solution in diethyl ether) are added to the reactor. After drying for 16 h at 50° C. in vacuo, an overpressure of 1.5 bar argon is applied and the reaction mixture is heated, accompanied by stirring for 25 min to 205° C. This temperature is maintained for 5 h. In the second stage addition takes place of 400 g of melted glycolide for forming the hard segenls under an argon counterflow and accompanied by vigorous stirring. The temperature is raised to 210° C. and kept there for a further 90 min.

The polymer has an inherent viscosity of 1.03 g/dl, its glass transition point is −15.7° C. and the melting point 102.3° C.

Example 10

Extrusion of the ABA-triblock terpolymer to a multifilament.

The triblock terpolymer of example 7 is melted by means of a single-screw extruder at a screw speed of 17 r.p.m. and spun to multifilaments. Use is made of a 24 capillary nozzle, the capillaries having a L/D ratio of 4:1 and a circular cross-section. The spinning head temperature is 202° C. Air is blown onto the fibres at a temperature of 20° C. for strengthening purposes. The distance between the nozzle and cooling section is 3 cm. The solid multifilaments are wound. The multifilaments are drawn by means of a draw-twisting machine, the multifilament being guided via drawing rolls and rails. The first rail is heated to 30° C. and the second to 45° C. The draw ratio for the first pass is 6.5:1 and for the second 1.2:1, which gives a total draw ratio of 7.8. To obtain an adequate dimensional stability the drawn threads are then annealed for 6 hours at a temperature of 90° C. in a further process stage. From the thermoset multifilament is produced a narrow fabric (atlas weave) with a width of 10 mm for use as an augmentation lielt.

Example 11

Extrustion of the ABA-triblock terpolymer to the multifilament.

The triblock terpolymer of example 8 is spun to a multifilament in accordance with example 10.

The process conditions for extrusion, drawing and annealing, as well as the mechanical characteristics of the multifilaments of examples 10 and 11 are given in the following table 1.

TABLE 1

|  | Example 10 | Example 11 |
| --- | --- | --- |
| Extrusion |  |  |
| Polymer | From Ex. 7 | From Ex. 8 |
| Screw speed (r.p.m.) | 17 | 15 |
| Spinning pump speed (r.p.m.) | 9 | 8 |
| Nozzle temperature (° C.) | 202 | 193 |
| Nozzle pressure (bar) | 95 | 87 |
| Capillary number | 24 | 24 |
| Capillary diameter ($\mu$m) | 200 | 200 |
| Cooling section temperature (° C.) | 20 | 20 |
| Draw-off speed (m/min) | 720 | 680 |
| Drawing |  |  |
| Draw ratio 1 | 6.5:1 | 5.7:1 |
| Temperature rail 1 (° C.) | 30 | 30 |
| Draw ratio 2 | 1.2:1 | 1.1:1 |
| Temperature rail 2 (° C.) | 45 | 40 |
| Total draw | 7.80 | 6.27 |
| Yarn titre (dtex) | 54.1 | 52.7 |
| Linear tensile strength (cN/tex) | 40.3 | 38.9 |
| Knot tensile strength (cN/tex) | 29.4 | 30.3 |
| Modulus of elasticity (cN/tex) | 60.7 | 55.0 |
| Elongation (%) | 34.8 | 38.7 |
| Annealing (no shrinkage) |  |  |
| Annealing time (h) | 6 | 6 |
| Temperature (° C.) | 90 | 90 |
| Yarn titre (dtex) | 53.8 | 52.6 |
| Linear tensile strength (cN/tex) | 44.6 | 40.1 |
| Knot tensile strength (cN/tex) | 33.3 | 34.5 |
| Modulus of elasticity (cN/tex) | 70.8 | 61.4 |
| Elongation (%) | 31.2 | 36.5 |

Example 12

Extrusion of the ABA-triblock terpolymer of example 6 to a film.

The triblock terpolymer of example 6 is extruded to a film by means of a twin-screw extruder and a slot die (width 3 cm, slot width 0.5 mm). The die temperature is 175° C. For strengthening purposes, the extruded film is drawn through a cooling bath with water at 20° C. The die-bath distance is 2 cm. The draw-off device is a driven godet wheel with pressing roller. The film then passes through a calendering device, whose rollers are heated to 35° C. The roller spacing is 0.20 mm, so that the end product has a thickness of 0.25 mm. The film is characterized by high flexibility and extensibility. It is therefore particularly suitable as an anti-adhesion film for preventing growing together, e.g. in the case of intestinal operations.

Example 13

Membraie production from ABA-triblock terpolymer by phase inversion technology.

The polymer of example 9 is 7 wt. % dissolved in chloroform. The filtered and deaerated solution is extruded by means of a piston-type spinning machine (T=30° C.) in conjunction with a slot die in a precipitating bath, comprising ethanol, and drawn off by a driven drum in said bath. The air gap is 0.5 cm and the precipitating bath temperature 22° C. The membrane is then dried for 48 h in high vacuum at 20° C. The membrane pore size varies between 1 and 9 pm and the membrane thickness is 53 pm. It is flexible and elastic and is therefore eminently suitable for periodontology, as a dermatoplasty or for guided tissue regeneration (GTR).

Example 14

Production of an injection moulding from the ABA-triblock terpolymer.

The triblock terpolymer of example 5 is moulded with an in-line screw-type injection moulding machine at a material temperature of 200° C., a mould mperature of 15° C. and an injection pressure of 340 bar to an anastomosis ring. The after-pressure during injection moulding is 150 bar to keep rinkage low. To improve the dimensional stability and increase crystallinity, the moulding obtained is annealed in two stages (5 h at 40 and then 7 h at 80° C.).

What is claimed is:

1. Triblock terpolymer with a structure ABA formed from a biodegradable hard segment A and a biodegradable soft segment B, in which the soft segment B is dihydroxy-terminated and chemically bound to the two hard segments A, wherein the soft segment is a statistical terpolymer formed from trimethylene carbonate, $\epsilon$-caprolactone and glycolide with a completely amorphous structure.

2. Triblock terpolymer according to claim 1, wherein the terpolymer in the soft segment B contains a monomer, which is contained in the hard segment A.

3. Triblock terpolymer according to claim 1, wherein the hard segment blocks contain 20 to 95 wt. % of the triblock terpolymer.

4. Triblock terpolymer according to claim 1, wherein the terpolymer of the soft segment B contains 5 to 70 wt. % trimethylene carbonate, 5 to 70 wt. % ϵcaprolactone and 10 to 70 wt. % glycolide.

5. Triblock terpolymer according to claim 1, wherein the terpolymer of the soft segment B contains trimethylene carbonate and ϵ-caprolactone in a weight ratio between 80:20 and 20:80.

6. Triblock terpolymer according to claim 1, wherein a monomer present in hard segment A is glycolide.

7. A medical product wholly or partly formed from an absorbable polymer comprising a triblock terpolymer with a structure ABA formed from a biodegradable hard segment A and a biodegradable soft segment B, in which the soft segment is dihydroxy-terminated and chemically bound to both hard segments A and the soft segment is a statistical terpolymer formed from trimethylene carbonate, ϵ-caprolactone and glycolide with a completely amorphous structure.

8. The medical product of claim 7 in the form of a film.

9. The medical product of claim 7 in the form of a microporous membrane.

10. The medical product of claim 7 in the form of an injection moulding.

11. The medical product of claim 7 in the form of a textile fabric.

12. Process for the production of a triblock terpolymer with a structure ABA formed from a biodegradable hard segment A and a biodegradable soft segment B, in which the soft segment is dihydroxy-terminated and chemically bound to the two hard segments A, wherein the triblock terpolymer is formed by chemically reacting the hard segment monomer with hydroxy terminal groups of soft segment B, which is a statistical terpolymer formed from trimethylene carbonate, ϵ-caprolactone and glycolide with a completely amorphous structure.

13. Process according to claim 12, wherein the soft segment contains 5 to 70 wt. % trimethylene carbonate, 5 to 70 wt. % ϵ-caprolactone and 10 to 70 wt. % glycolide.

14. Process according to claim 13, wherein the soft segment contains 10 to 40 wt. % trimethylene carbonate, 10 to 40 wt. % ϵ-caprolactone and 30 to 50 wt. % glycolide.

15. Process according to claim 12, wherein the triblock terpolymer is treated with γ-rays.

* * * * *

UNITED STATES PATENT AND TRADEMARK OFFICE
CERTIFICATE OF CORRECTION

PATENT NO. : 6,031,069

DATED : February 29, 2000

INVENTORS : Sven OBERHOFFNER et al.

It is certified that error appears in the above-identified patent and that said Letters Patent is hereby corrected as shown below:

Column 13, line 3: change "ϵcaprolactone" to --ϵ-caprolactone--.

Column 13, line 18: change "ϵ-caproIactonc" to --ϵ-caprolactone--.

UNITED STATES PATENT AND TRADEMARK OFFICE
CERTIFICATE OF CORRECTION

PATENT NO. : 6,031,069
DATED : February 29, 2000
INVENTOR(S) : Sven OBERHOFFNER et al.

It is certified that error appears in the above-identified patent and that said Letters Patent is hereby corrected as shown below:

Column 13, line 20: renumber claim "8" as claim --7--; and change the claim dependency from claim "7" to claim --6--.

Column 13, line 21: renumber claim "9" as claim --8--; and change the claim dependency from claim "7" to claim --6--.

Column 13, line 23: renumber claim "10" as claim --9--; and change the claim dependency from claim "7" to claim --6--.

Column 14, line 1: renumber claim "11" as claim --10--; and change the claim dependency from claim "7" to claim --6--.

Column 14, line 3: renumber claim "12" as claim --11--.

Column 14, line 13: renumber claim "13" as claim --12--; and change the claim dependency from claim "12" to claim --11--.

Column 14, line 16: renumber claim "14" as claim --13--; and change the claim dependency from claim "13" to claim --12--.

Column 14, line 19: renumber claim "15" as claim --14--; and change the claim dependency from claim "12" to claim --11--.

UNITED STATES PATENT AND TRADEMARK OFFICE
CERTIFICATE OF CORRECTION

PATENT NO. : 6,031,069
DATED : February 29, 2000
INVENTOR(S) : Sven OBERHOFFNER et al.

It is certified that error appears in the above-identified patent and that said Letters Patent is hereby corrected as shown below:

Add the following new claims:

--15. The triblock terpolymer according to claim 1, wherein the hard segment blocks contain 40-60 wt. % of the triblock terpolymer.--

--16. The triblock terpolymer according to claim 1, wherein the soft segment contains 10 to 40 wt.% trimethylene carbonate, 10 to 40 wt.% ε-caprolactone and 30 to 50 wt.% glycolide.--

--17. The triblock terpolymer according to claim 1, wherein the hard segment A blocks contain a glycolide monomer and represent 20 to 95 wt.% of the triblock terpolymer, the soft segment B contains 5 to 70 wt.% trimethylene carbonate, 5 to 70 wt.% ε-caprolactone and 10 to 70 wt.% glycolide with trimethylene carbonate and ε-caprolactone in a weight ratio between 80:20 and 20:80 and the terpolymer has a glass transition temperature in the range of -10 to 30°C and a melting point which is greater than 120°C.--

--18. The process according to claim 11, wherein the hard segment comprises glycolide monomer and the soft segment is reacted with the glycolide by repeated melting of the soft segment with glycolide at a temperature of between 200 and 250°C, optionally in the presence of a catalyst and/or a bifunctional initiator, with stirring and an over pressure of between 1 and 2 bar argon, for a sufficient time to produce the triblock terpolymer; and the process further comprising the steps of:
    preparing the soft segment B by statistically copolymerizing 5 to 70 weight percent trimethylene carbonate, 5 to 70 weight percent ε-caprolactone and 10 to 70 weight percent glycolide, optionally in the presence of a catalyst and/or a bifunctional initiator, at a temperature above 150°C so that the mixture is a melt, with stirring and an over pressure of between 1 and 2 bar argon for a sufficient time to produce the soft segment;
    recovering the soft segment material; and
    recovering the triblock terpolymer material.--

--19. The process according to claim 18, wherein the soft segment is recovered by discharging the soft segment from the reactor, cooling the soft segment and comminuting the soft segment material, and the triblock terpolymer is recovered by discharging the triblock terpolymer from the reactor, cooling the triblock terpolymer, comminuting the triblock terpolymer, and then drying the triblock terpolymer.--

UNITED STATES PATENT AND TRADEMARK OFFICE
CERTIFICATE OF CORRECTION

PATENT NO. : 6,031,069
DATED : February 29, 2000
INVENTOR(S) : Sven OBERHOFFNER et al.

It is certified that error appears in the above-identified patent and that said Letters Patent is hereby corrected as shown below:

--20. The process according to claim 11, wherein the hard segment comprises glycolide monomer and the soft segment is reacted with the glycolide by adding to the soft segment in a polymerization reactor glycolide monomer as a melt under an argon counterflow, with vigorous stirring, raising the temperature to about 230°C in less than 15 minutes, reducing the temperature to 220°C and allowing the reaction to proceed for sufficient time to form the triblock terpolymer; and the process further comprising the steps of:

preparing the soft segment B in the polymerization reactor by statistically copolymerizing trimethylene carbonate, ε-caprolactone, and glycolide, in the presence of a catalyst and an initiator, at a temperature between 200 and 210°C with stirring and with an over pressure of between 1 and 2 bar argon for a sufficient time to produce the soft segment; and recovering the triblock terpolymer by discharging the triblock terpolymer from the reactor, cooling the triblock terpolymer, comminuting the triblock terpolymer, and drying the triblock terpolymer.

--21. The triblock terpolymer according to claim 1, wherein the hard segment A blocks contain a glycolide monomer and represent 20 to 95 wt.% of the triblock terpolymer, the soft segment B contains 5 to 70 wt.% trimethylene carbonate, 5 to 70 wt.% ε-caprolactone and 10 to 70 wt.% glycolide with trimethylene carbonate and ε-caprolactone in a weight ratio between 80:20 and 20:80.--

--22. The triblock terpolymer according to claim 1, wherein the hard segment A blocks contain a glycolide monomer and represent 20 to 95 wt.% of the triblock terpolymer, the soft segment B contains 5 to 70 wt.% trimethylene carbonate, 5 to 70 wt.% ε-caprolactone and 10 to 70 wt.% glycolide with trimethylene carbonate and ε-caprolactone in a weight ratio between 80:20 and 20:80 and the terpolymer has a glass transition temperature in the range of -10 to 25°C.--

UNITED STATES PATENT AND TRADEMARK OFFICE
CERTIFICATE OF CORRECTION

PATENT NO. : 6,031,069
DATED : February 29, 2000
INVENTOR(S) : Sven OBERHOFFNER et al.

It is certified that error appears in the above-identified patent and that said Letters Patent is hereby corrected as shown below:

--23. The triblock terpolymer according to claim 1, wherein the hard segment A blocks contain a glycolide monomer and represent 20 to 95 wt.% of the triblock terpolymer, the soft segment B contains 5 to 70 wt.% trimethylene carbonate, 5 to 70 wt.% ε-caprolactone and 10 to 70 wt.% glycolide with trimethylene carbonate and ε-caprolactone in a weight ratio between 80:20 and 20:80 and the terpolymer has a glass transition temperature in the range of -10 to 25°C and a melting point which is at least 164.5°C.--

Signed and Sealed this

Twenty-seventh Day of February, 2001

Attest:

NICHOLAS P. GODICI

Attesting Officer

Acting Director of the United States Patent and Trademark Office